United States Patent [19]
Domb et al.

[11] Patent Number: 5,512,055
[45] Date of Patent: *Apr. 30, 1996

[54] ANTI-INFECTIVE AND ANTI-INFLAMMATORY RELEASING SYSTEMS FOR MEDICAL DEVICES

[75] Inventors: Abraham J. Domb; Alain Shikani; Andrew S. T. Haffer; Manoj Maniar, all of Baltimore, Md.

[73] Assignee: Leonard Bloom, Towson, Md.; a part interest

[*] Notice: The term of this patent shall not extend beyond the expiration date of Pat. No. 5,344,411.

[21] Appl. No.: 316,067

[22] Filed: Sep. 30, 1994

Related U.S. Application Data

[63] Continuation of Ser. No. 998,773, Dec. 22, 1992, abandoned, which is a continuation of Ser. No. 661,699, Feb. 27, 1991, abandoned.

[51] Int. Cl.$^6$ ..................................... A61M 5/32
[52] U.S. Cl. ................ 604/265; 604/891.1; 128/207.14; 623/11
[58] Field of Search ................... 128/207.14, 207.15; 604/890.1, 891.1, 892.1, 264, 280, 265; 623/1, 11, 12

[56] References Cited

U.S. PATENT DOCUMENTS

| | | | |
|---|---|---|---|
| 4,381,380 | 4/1983 | Lambert et al. | 604/265 |
| 4,642,104 | 2/1987 | Sakamoto et al. | 604/265 |
| 4,650,488 | 3/1987 | Bays et al. | 604/265 |
| 4,879,135 | 11/1989 | Greco et al. | 623/12 |
| 4,917,686 | 4/1990 | Bayston et al. | 604/265 |
| 4,994,047 | 2/1991 | Walker et al. | 604/265 |
| 5,013,306 | 5/1991 | Solomon et al. | 604/265 |
| 5,019,096 | 5/1991 | Fox, Jr. | 604/265 |
| 5,019,601 | 5/1991 | Allen | 604/96 |
| 5,028,597 | 7/1991 | Kodama et al. | 623/12 |
| 5,061,254 | 10/1991 | Karakelle et al. | 604/265 |
| 5,102,401 | 4/1992 | Lambert et al. | 604/264 |
| 5,165,952 | 11/1992 | Solomon | 604/265 |
| 5,344,411 | 9/1994 | Domb et al. | 604/265 |

OTHER PUBLICATIONS

*The Merck Index: An Encyclopedia of Chemicals, Drugs and Biologicals,* tenth edition (1983) pp. 425 & 1373.
Shah, et al., *J. Surg. Res.* 42, 298–303 (1987).
Rushton, et al., *J. Neurology, Neurosurgery and Psychiatry* 52:223–229 (1989).
Watanabe, et al., *Artif. Organs* 9(3), 334–335.
Baxter Travenol Laboratories, S. African ZA 85 07,530, *Chem. Abstracts* 107:64897h (Aug. 1987).
Unitika Ltd., Jpn. Kokai Tokyo Koho JP 61,146,265 *Chem. Abstracts* 105:197229x (Dec. 1986).
Devi and Vasudevan, *Rev. Macromol. Chem. Phys.* C25(3), 315–324 (1985).
"Antimicrobial Rubber Gloves Offer Added Protection" *Biomedical Materials* (Jul. 1990).

Primary Examiner—C. Fred Rosenbaum
Assistant Examiner—Chalin Smith
Attorney, Agent, or Firm—Leonard Bloom

[57] ABSTRACT

Devices are provided having a polymer coating incorporating compounds inhibiting inflammation and infection, along with subsequent tissue growth onto and around the device. Preferred embodiments include catheters, tubes, and implants that abut tissue following implantation into the body, especially for use in the naso-oto-pharyngeal areas of the body, where localized chronic infection/inflammation of the tissues surrounding the implant may be decreased by sustained release of antibiotics, antifungals, antivirals, anti-inflammatories, and other compounds, such as anticoagulants and anesthetics. Preferred polymeric coatings are thin, well adhered to the underlying device, and formed of a biocompatible, non-bioerodible polymer such as polyurethane or ethylene vinyl acetate. The drug is incorporated either by solvent casting or by absorption into the solidified polymer. The drug incorporated polymer can also be used to form devices, or portions of devices, for implantation.

9 Claims, 5 Drawing Sheets

ANTI-INFECTIVE AND ANTI-INFLAMMATORY RELEASING SYSTEMS FOR MEDICAL DEVICES

This application is a continuation of application Ser. No. 998,773, filed Dec. 22, 1992, now abanboned, which is a continuation of application Ser. No. 661,699, filed Feb. 27, 1991, now abandoned.

BACKGROUND OF THE INVENTION

This invention relates to invasive medical devices for delayed/sustained release of pharmaceutical compositions from a polymer that is coated or incorporated into the devices. The purpose of the coating or delivery system on these devices is to reduce, control or even prevent the inflammation and infection that occur with prolonged use of these devices.

A longstanding problem is in the area of medical devices directly contacting the mucosa and the tissue of the body for prolonged periods of time, thereby causing a reaction by the body against those devices, as is the case with tracheotomy tubes, endotracheal tubes, tracheal tubes, stoma stents, laryngeal/bronchial stents, laryngeal keels, esophageal reconstruction tubes, nasal/paranasal tubes or splints, nasogastric tubes, ear ventilation (PE) tubes, gastrostomy tubes, foley catheters, intravenous catheters and all kinds of indwelling percutaneous catheters. This reaction often consists of an inflammation and/or infection that frequently progresses into a pathological process. There is also a longstanding problem with infection associated with this process.

For example, prolonged intubation using endotracheal tubes or tracheotomy tubes may cause subglottic stenosis. Acquired subglottic stenosis consequent to prolonged intubation is a much dreaded and morbid condition. This disease is reported to develop in 4% to 8% of those infants and neonates who require sustained intubation, as described by Marshak G., et al., *Pediatr. Clin. North Am.* 28: 941–948 (1981). In both adults and children, the incidence is increasing with increasing survivorship in intensive care units. The pathophysiology of acquired subglottic stenosis is well known, for example, as described by Cotton, R. T., et al: In Paparella and Shumrick, editors, *Otolaryngology*, Vol. II: Chronic laryngeal and tracheal stenosis (W. B. Saunders, Philadelphia, 1980); Hawkins, D. B. *Laryngoscope* 87:339 (1977); and Biller, H. F. et al, *Ann. Otol. Laryngol.* 79: 1084–7 (1970).

The endotracheal tube causes pressure necrosis at the point of interface with tissue, leading to mucosal edema and ulceration. As ulceration deepens, there is an interruption of normal ciliary flow with mucociliary stasis leading to secondary infection and perichondritis, as reviewed Sasaki, C. T., et al., *Laryngoscope* 89:857–865 (1979). With further infection, chondritis and cartilaginous necrosis occur, especially with collapse of the airway during inspiration. Healing occurs by secondary intention in the areas of ulceration and deposition of fibrous tissue in the submucosa, leading to subglottic stenosis.

The management of this problem is both controversial and frustrating, as evidenced by the wide spectrum of therapeutic procedures advocated, and the fact that all of them give far from ideal results. Of the non-invasive treatment modalities available, administration of corticosteroids, alone or with systemically administered antibiotics has been advocated by Borowiecki, B., et al, *Ann. Otol. Rhinol. Laryngol,* 86:835–40 (1977); and Suspance, *J. Ann. Otol. Rhinol. Laryngol.* 92: 377–382 (1983). Corticosteroids are known to have an anti-inflammatory effect on the exudative and destructive phases of injury as well as during the period of healing. Since the basic principle in prevention is to control, reduce or even prevent submucosal fibrosis, systemic steroids have been administered to reduce inflammation during the exudative and destructive phase of tissue injury, and in the period of healing or scarring, or both. Furthermore, recently, inhaled aerolized corticosteroids have been shown to be quite beneficial in reducing the subglottic injury in animals, Kryzer, T. C., et al: "Effects of aerolized Dexamethasone on acute subglottic injury", presented at the Fourth Annual Symposium of the Uniformed Services University of Health Services (Bethesda, Md., May 1990). The drawback to systemic steroid treatment is that it results in a generalized immunosuppression and decrease in healing, as well as other undesirable side effects.

Antimicrobial therapy has been advocated to control localized subglottic bacterial infection, which has been suggested as contributing to the progression of the disease. Experimental studies in dogs have shown that the timing and duration of therapy after injury are of great importance in reducing the activity and sequelae of sclerosing chondritis, as reported by Croft, C., et al, *Laryngoscope* 89:482–489 (1979). With the continuous presence of the endotracheal or tracheotomy tube, granulation tissue may occur, not only perpetuating the local infection but also sometimes blocking the airway and necessitating emergency surgical intervention. Experimental studies in animals have shown that the key in this form of treatment is to achieve a high local concentration of antibiotics and to maintain the treatment throughout the period of intubation, Kryzer, T. C., (1990). This, until now, has not been the standard of clinical care because of the cost and the potential systemic side effects of such prolonged treatment and of technical difficulties, as some patients remain intubated for months.

Every patient who is intubated or undergoes a tracheotomy runs the risk of developing subglottic stenosis. This is especially true for the pediatric population who has a relatively narrow airway and is susceptible to airway compromise even with minor subglottic inflammation. To understand the magnitude of the problem, a review of the records on tracheotomy and prolonged endotracheal intubation was completed from the Vital & Health Statistics data collection. In 1973, 42,000 tracheotomies were performed in the United States alone; extrapolating to 1990, 65,000 were done in the USA. Of these, especially in children, a large number will develop mucosal inflammation and stomal granulation tissue if the tube is left long enough (in children almost all will get this problem and one half of them need some kind of surgical intervention for the granulation tissue). A much larger number of patients are expected to undergo prolonged intubation, especially with the introduction of improved intensive care units. The exact number of these patients is not available; although about 4,000,000 surgical procedures necessitating intubation were done in 1973 in the United States alone.

Another long standing problem of significance is chronic nasal and paranasal disease, with a prevalence of about 40 million people in the United States alone. Endoscopic sinus surgery is being increasingly done in these patients with the availability of new telescopic instruments and comprehensive training in the field. The most common complication of this operation is scarring and stenosis. There are no truly effective means to prevent or treat this problem.

Still another problem involving treatment of the nasopharyngeal region of the body is the treatment of caustic burns to the esophagus. The most common cause of esophageal stricture in children is the accidental ingestion of strong corrosive agents, as reported by Haller, J. A., et al, *J. Ped. Surg.* 6(5): 578–584 (1971). In adults and teenagers, caustic injuries occur as a result of an attempt at suicide. By far the most common agent ingested is concentrated sodium hydroxide in the form of commercial toilet bowl and oven cleaners. The result of the ingestion is severe inflammation combined with ulceration, vascular thrombosis and liquefaction necrosis, which may lead to varying degrees of stricture formation.

In the past, treatment was based on repeated and continuing esophageal dilation to prevent ultimate severe strictures, although this has been abandoned. In its place, an indirect treatment was introduced, which consists of systemic administration of corticosteroids to decrease the inflammatory reaction, and antibiotics to help prevent secondary infection. Animal studies have shown that after the acute inflammatory reaction, fibroblasts proliferate over the next two to three weeks, and healing is complete by the end of that time, as reported by Haller, J. A., *Pediatrics* 34(2): 236–245 (1964). Based on these studies, the prophylactic use of systemic steroids and antibiotics is for the first week to 10 days, with a continuation of systemic steroids for protection against inflammation and fibroblast proliferation for the full three weeks, as described by Haller, et al., (1964); Haller, J. A,, "Caustic burns of the esophagus". *Current Therapy in Cardiothoracic Surgery,* pp.75–76 (B. C. Becker Inc., 1989).

Another approach to the management of this injury has included the use of an intraluminal esophageal stent to prevent stricture formation. As described by Tucker, J. A. *Otol. Clinics North Amer.* vol.12, 343–349 (1979), the stent used for adults was a 47 cm silicone tube with a ⅝ inch outside diameter which was kept in place for about 3 weeks. As with the other procedures, the treatment and results are still less than adequate.

Other problems in this area include ear ventilation (PE) tubes. Millions of PE tubes are inserted every year in the United States alone. Of all PE tubes, 20% result in chronic otorrhea and require systemic antibiotics. Those who fail to respond to the systemic antibiotics, sometimes respond to local installation of antibiotics and corticosteroids introduced into the middle ear through the tube. A certain number will need removal of the tube, as reported by Bluestone and Stool, *Pediatric Otolaryngology,* pp. 321–486, 2nd edition (Saunders Publishing Co, Philadelphia 1990).

The sustained release of biologically active agents from polymers has been shown to be effective in several systems, including implants, ocular inserts, coated intrauterine devices and other similar devices, as described in U.S. Pat. Nos. 3,416,530 to Ness; 3,55,556 to Kliment, et al.; 4,548, 990 to Mueller, et al. and 4,888,413 to Domb. In the preferred embodiments, these have utilized bioerodible polymers as the matrix for the drug to be released, usually as a function of diffusion and erosion of the polymer. The advantage of these drug delivery systems is that they provide a sustained/continuous release of drugs locally and at a relatively high concentration in areas of the body, without systemic side-affects, throughout the duration of their release.

Efforts to incorporate antibiotic releasing coatings into catheters have been made. U.S. Pat. No. 4,950,256 to Luthoer and Shanbrom discloses an intravascular catheter having a polymeric coating incorporating an antibiotic. The antibiotic prevents bacterial growth on the catheter when inserted into a blood vessel of the patient. U.S. Pat. No. 3,598,127 to Wepsic discloses a urinary tract catheter formed of a nonpermeable rubber coated with an antibiotic surrounded by an outer coating of a permeable rubber coating through which the antibiotic can diffuse. However, no one has addressed the more difficult problem of inflammation and growth of tissue around a catheter.

It is therefore an object of the present invention to provide medical devices which are anti-microbial and anti-inflammatory.

It is a further object of the present invention to provide medical devices having prolonged low-dose, localized release of anti-microbial and anti-inflammatory agents.

It is a still further object to provide medical devices for insertion or implantation into tissue that are resistant to infection and inhibit inflammation and growth of tissue around and onto the device.

SUMMARY OF THE INVENTION

Devices are provided having a polymer coating incorporating compounds inhibiting inflammation and infection, along with subsequent tissue growth onto and around the device. Preferred embodiments include catheters, tubes, and implants that abut tissue following implantation into the body, especially for use in the naso-oto-pharyngeal areas of the body, where localized chronic infection/inflammation of the tissues surrounding the implant may be decreased by sustained release of antibiotics, antifungals, antivirals, anti-inflammatories, and other compounds, such as anticoagulants and anesthetics.

Preferred polymeric coatings are thin, well adhered to the underlying device, and formed of a biocompatible, non-bioerodible polymer such as polyurethane or ethylene vinyl acetate. The drug is incorporated either by solvent casting or by absorption into the solidified polymer. The drug incorporated polymer can also be used to form devices, or portions of devices, for implantation.

DETAILED DESCRIPTION OF THE INVENTION

Devices are provided having a polymer coating incorporating compounds inhibiting inflammation and infection, along with subsequent tissue growth onto and around the device. Preferred embodiments include catheters, tubes, and implants for use in the naso-oto-pharyngeal areas of the body where localized chronic infection/inflammation of the tissues surrounding the implant may be decreased by sustained release of antibiotics, antifungals, antivirals, anti-inflammatories, and other compounds, such as anticoagulants and anesthetics.

In a particularly preferred embodiment, polymers incorporating steroids are coated onto devices including tracheal T-tubes, stoma stents, laryngeal/bronchial stents, laryngeal keels, and nasogastric tubes. It appears that the corticosteroids/antibiotics combination, administered at the onset of injury (i.e., time of intubation) and throughout the duration of the intubation may prevent the development of subglottic stenosis. The drug-loaded polymer provides a sustained release of steroids and antibiotics locally and at a relatively high concentration in that area which is critically affected, without the side-effects of the systemic administration of the same drugs, throughout the duration of the intubation.

In other embodiments, the coatings are applied to devices used in the nasal airway and paranasal sinuses, e.g., nasal splints and paranasal ventilation tubes. Scarring and stenosis can be decreased or avoided by using long-term silicone-made sinus ventilation tubes incorporating polymers for sustained release of corticosteroids and antibiotics to reduce the inflammation and infection caused by the healing sinuses and decrease the reaction of the body to the sinus tubes.

In yet another embodiment, antifungal drugs are incorporated into the polymer for the treatment of fungal sinusitis, thereby minimizing the relatively high incidence of side-effects that occur when systemic anti-fungal drugs are administered avoided by local delivery within the nose/paranasal sinuses. An esophageal silicone stent coated with a film of polymer can be used to provide a site-specific controlled release of corticosteroids and antibiotics. Coating that part of the tube, which is in contact with the mucosa, with the drug-loaded polymer provides a sustained release of steroids and antibiotics locally and at high concentration in the area which is critically affected, achieving the same effect as the systemic administration of the drugs without their side-effects, throughout the duration of the intubation. This stent is generally removed at the end of the three weeks.

Coating with or manufacturing the inner flange of a PE tube (the side within the middle ear) a polymer that releases corticosteroids and antibiotics provides a sustained local treatment, decreasing the severity and frequency of the otorrhea in some cases.

Catheters and all kinds of percutaneous catheters used for long-term delivery of intravenous fluids (e.g., Swan-Ganz catheters, double and triple lumen central catheters, arterial line monitoring catheters, and others, including foley catheters that are used for long-term bladder intubation), as well as tubes and other devices that contact tissue, rather than fluid, can be coated with anti-inflammatory coatings and local anesthetics to decrease pain and inflammation during use. Coating the catheters with an antibiotic-releasing catheter would also decrease bacterial colonization and subsequent infection at the site of catheter introduction.

The polymer coatings are formed by methods known to those skilled in the art, such as solvent casting or melting. They are preferably between 1.0 and 0.01 mm in thickness, most preferably between 0.5 and 0.01 mm in thickness. The polymers should be biocompatible and non-erodible. Examples of suitable polymers include ethylene vinyl acetate, polyurethane, silicones, hydrogels, polyurethane, and polyvinyl chloride. In the preferred embodiments, the coatings are uniform and transparent, smooth and very thin (<0.1 mm), and adhere very well to the surface of the device, even after implantation in vivo and longer term immersion in fluids.

Similar methods can be used to form all or part of devices incorporating drugs such as anti-infectives, anti-inflammatories, anesthetics and anticoagulants. The drugs to be released can be incorporated at the time of manufacture or subsequently, by absorption.

The biologically active agent to be released is incorporated at the time of casting or melting, or subsequently, by absorption, with both the coatings and the devices, in whole or in part. The process should yield a polymer releasing the incorporated agent over a prolonged period of time, greater than one day and extending up to several days or weeks. Release is a function of diffusion of the agent from the polymeric matrix, and varies by size, concentration and solubility of the agent, as well as by thickness and chemical composition of the polymeric matrix.

Anti-inflammatories that can be incorporated into the polymeric coatings include steroids and non-steroidal anti-inflammatories. For example, corticosteroids can be dexamethasone, hydrocortisone, triamcinolone, methylprednisolone or analogs thereof. Non-steroidal antiinflammatories include compounds such as cyclosporin, ibruprofen, and naproxen. The anti-infectives include antibiotics, antifungals, and antivirals. Exemplary antibiotics include penicillins, cephalosporins, clindamyicin, aminoglycosides, tetracyclines and others. Exemplary antifungals are nystatin, lotrimin, ketoconazole, amphotericin B and analogs thereof. Antivirals include idoxuridine, amantadine, vidarabine, interferon, acyclovir, and analogues thereof.

The polymeric coatings can also be used as a delivery system for iodine. Although iodine is frequently administered by means of a sponge into which it has been absorbed or by means of a polymeric complex in which it has been reacted with the polymer, such as polyvinylpyrrolidone, it has not been incorporated into a thin polymeric matrix for controlled, prolonged release over an extended period of time.

Other compounds that can be incorporated into the polymer include anticoagulants such as heparin, or anesthetics, preferably topical anesthetics such as lidocaine.

The present invention will be further understood by reference to the following non-limiting examples.

EXAMPLE 1

Release of Nystatin from a coated tracheal tube

The tip of a tracheal tube device was coated as follows: 18% w/w nystatin (1 mg, 5,000 Units) in an ethylenevinyl acetate (EVA) coating was prepared by dipping the tip (up to the balloon, total area of coating 15 cm$^2$) of a tracheal tube, size 8.5 mm, style XL (Portex Inc., Wilmington, Mass.) in a 10 weight % EVA solution containing 18 weight % nystatin in dichloromethane. Solvent was evaporated to yield a 0.24 mm thick coating. The coating was overlaid with a thin layer (0.05 mm) of drug free EVA to slow the drug release.

Figure 1:
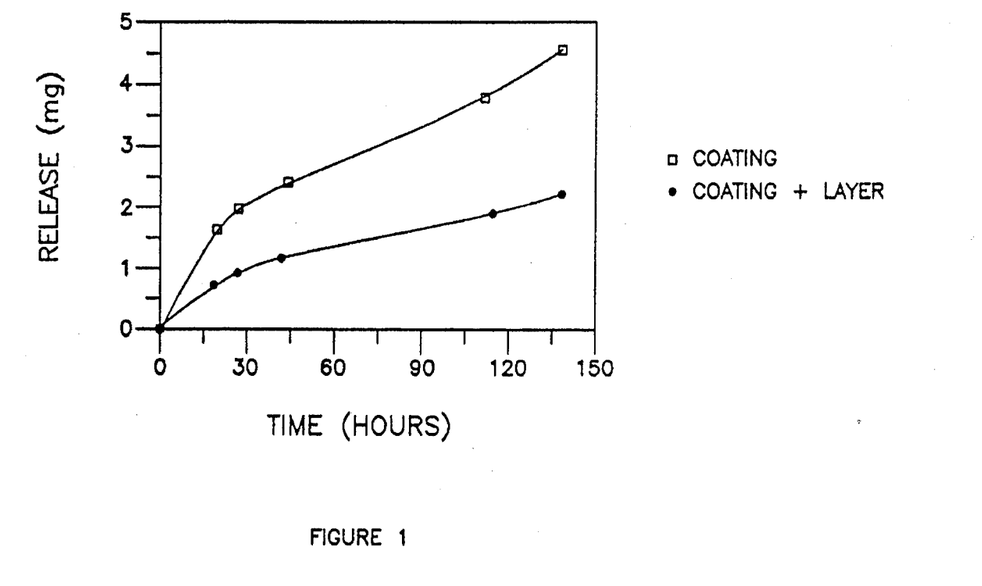
FIG. 1 is a graph of the release of nystatin (mg) over time (hours) from a tracheal tube coated with ethylene vinyl acetate (EVA) containing 18 weight % nystatin (squares) and the same tube overlaid with non-drug loaded EVA (dark diamonds).

Nystatin release from the tube was determined in 0.1M phosphate buffer pH 7.4 at 37° C., by measuring ultraviolet (UV) absorbance at 250 nm. The release of nystatin from coated and uncoated devices is shown in FIG. 1. As seen, 4.5 mg of drug is released from the coated tube. The release rate is decreased by further coating of the tube with a plain layer of EVA. The release can be increased or decreased by changing the drug loading or using different polymeric material for coating.

EXAMPLE 2

In vitro Release of Antimicrobial Iodine from a polymer coated Tracheal Tube

Iodine is a widely used broad spectrum antimicrobial agent. It is used in solutions, soaps, creams, paste, etc. A tracheal tube was coated with an iodine releasing system, as follows: 0.5 grams of iodine crystals were dissolved in tetrahydrofuran solution containing 1.5 grams of segmented polyurethane, PU (Estain™, Goodrich, Ill.). The tip of a tracheal tube, size 5.5 mm (Portex Inc., Wilmington, Mass.) was coated by dipping the tip in the iodine/polymer solution (total area of coating 3 cm$^2$). After solvent evaporation, the resulting dark uniform coating of about 0.2 mm was coated with an EVA coating by dipping in a chloroform solution of EVA. The EVA coating of 0.05 mm is to prevent iodine release from the surface by sublimation.

Figure 2:
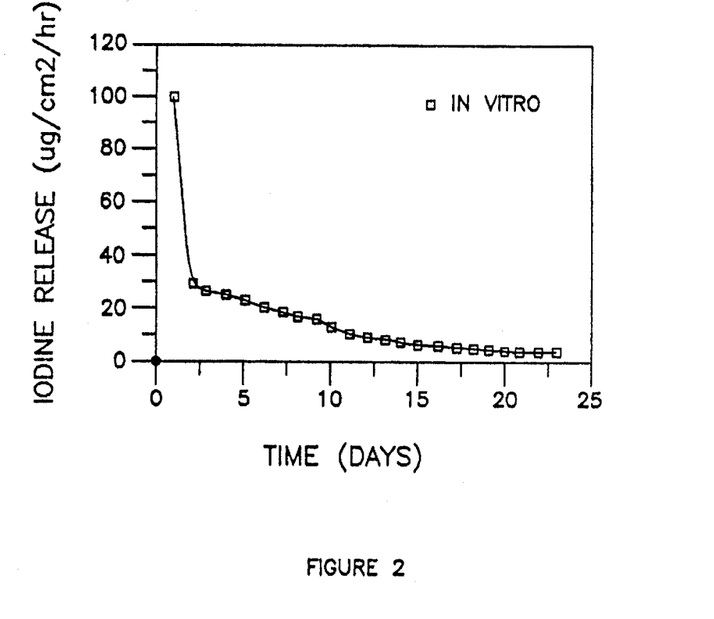
FIG. 2 is a graph of iodine release (μg/cm$^2$/hr) from a catheter having a polyurethane coating containing iodine, overlaid with non-drug loaded EVA, over time (days).

Alternatively, the tube was first coated with plain (non-drug loaded) polyurethane and then loaded with iodine by immersing the coated tube in a 20% I$_2$/KI solution in water. The impregnated PU/iodine coating was then dried in room air and coated with plain EVA. In vitro iodine release was determined in a 0.1N KI solution at 37° C. by measuring UV absorption at 310 nm. The release of iodine from the tube is shown in FIG. 2.

EXAMPLE 3

In Vivo and Biological Activity of Iodine Released from Tube Coating

Devices of iodine coated tubes, cut from a PVC tracheal tube, as prepared in Example 2, were subcutaneously implanted in six rats (two groups of three rats). The first group of three animals were sacrificed at day 7 and the devices were removed and placed for three consecutive days on an agar plate for antibacterial activity test as described below. At day 10 the tubes were placed in 20 ml 0.1N KI solution to measure release in vitro. The antimicrobial activity was determined again at day 16. The second group of 3 rats were sacrificed at day 14 and the antimicrobial activity and the in vitro release from the devices were determined. The antimicrobial activity was determined using agar plates (Bactopepton 1%, yeast extract 0.5%) seeded with pathogenic Staphylococcus aureus (removed from a catheter implanted in a patient). The tubes were placed on the agar plate and incubated for 24 hours and the inhibition zone was measured. The agar plates were replaced with fresh plates daily. The results are summarized in Table 1. As seen, the drug release decreases exponentially with time, but significant amounts of iodine are still being released from the devices even after 23 days in vitro. All devices were active against bacteria for 21 days. The drug release from the implanted devices after removal from the animals was lower, as compared with the in vitro data, which indicates that iodine is released faster in vivo. Histology of the site of implantation showed no irritation or necrosis was caused by the devices.

TABLE 1

In vitro, in vivo, and antibacterial activity of iodine coated tubes.

| Time (days) | In vitro (µg/cm$^2$/hr) | In vivo (7 days) | In vivo (14 days) | Antibacterial activity (mm) |
| --- | --- | --- | --- | --- |
| 1 | 108 | I | I | 65* (no growth) |
| 2 | 25 |  | N | 65* (no growth) |
| 3 | 23 |  |  | 55* |
| 4 | 23 | V | V | 52* |
| 5 | 21 | I | I | 45* |
| 6 | 19 | V | V | 12# |
| 7 | 18 | O | O | 12# |
| 8 | 16 | 35* |  | 10# |
| 9 | 16 | 30* |  | 9# |
| 10 | 12 | 7# |  | 8# |
| 11 | 10 | 7# |  | 8# |
| 12 | 9 | 6# |  | 7# |
| 13 | 8 | 6# |  | 5# |
| 14 | 7 | 30* | 27* | 32* |
| 15 | 6 | 27* | 25* | 30* |
| 16 | 5 | 5.6# | 28* | 4.2# |
| 17 | 5 | 4.7# | 27* | 3.5# |
| 19 | 4 | 3.3# | 2.6# | 2.3# |
| 21 | 4 | 3.1# | 1.4# | 2.0# |
| 23 | 4 | 3# | inactive | inactive |

*Diameter of inhibition zone, mm
In vitro iodine release, (µg/cm$^2$/hr)

EXAMPLE 4

Tetracycline-HCl Release From Silicon and EVA Films

Drug was incorporated into a silicone polymer for subsequent release. The silicon polymer can be used to prepare various silicone tubings and implantable devices, and portions thereof, of various sizes and shapes.

Silicone devices were prepared using Medical Grade elastomer (Dow Corning) and a curing agent (Dow Corning) mixed at a ratio of 10:1. To the mixture was added 10,25 w/w tetracycline-HCl and mixed well to form a yellow uniform mass. The mixture was cast into a 1 mm film and cured for 24 hours at room temperature. The film was cut into 5×5 mm slabs which weighed 50 mg each.

Ethylene Vinyl Acetate (EVA) devices were prepared by mixing 10 and 25% tetracycline-HCl in the polymer and casting to form a 1 mm film. The film was cut into 5×5 mm slabs which weighed 50 mg each.

Figure 3:
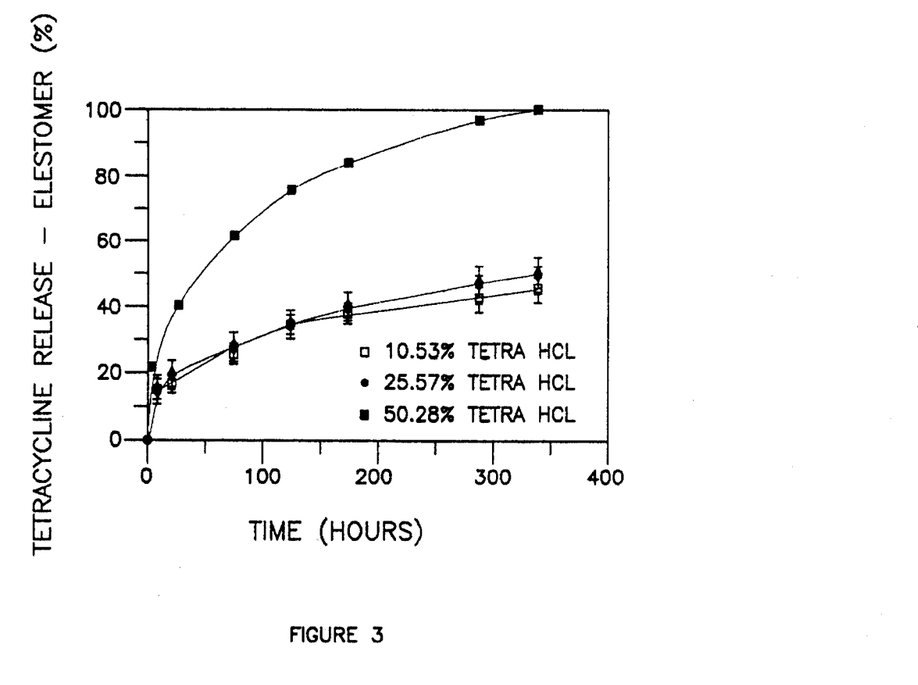
FIG. 3 is a graph of percent of tetracycline release from silicon coatings over time (hours) for 10.53% tetracycline-HCl (squares); 25.57% tetracycline-HCl (dark diamonds); and 50.28% tetracycline-HCl (dark squares).
Figure 4:
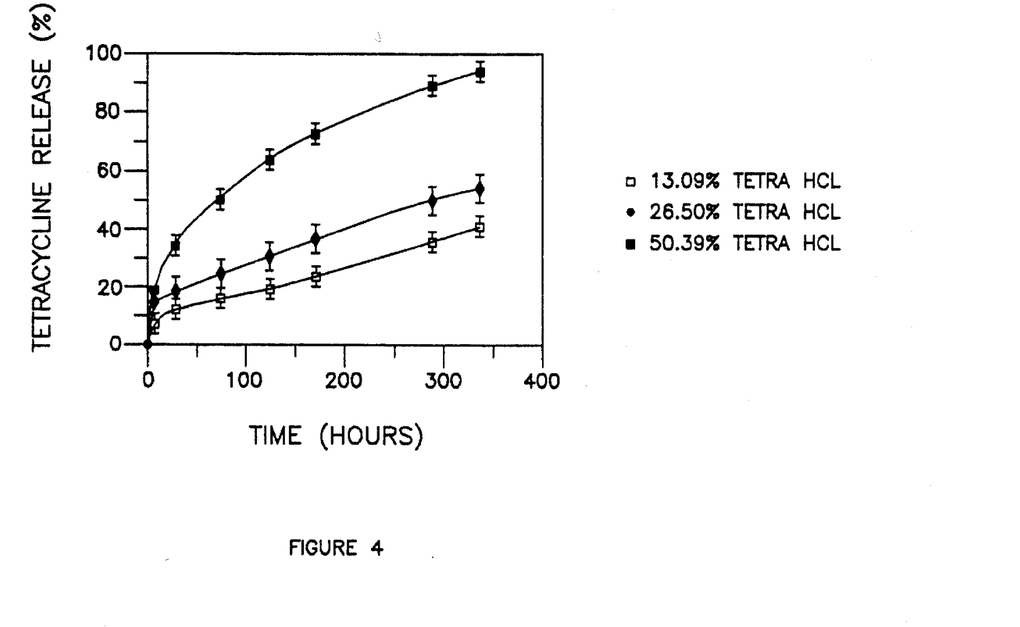
FIG. 4 is a graph of percent of tetracycline release from EVA coatings over time (hours) for 13.09% tetracycline-HCl (squares); 26.50% tetracycline-HCl (dark diamonds); and 50.39% tetracycline-HCl (dark squares).

The release of the drug from these devices (12 mg each) were studied in phosphate buffer pH 7.4 at 37° C. for 332 hours. Tetracycline was determined by measuring UV absorbance at 275 nm. The results are summarized in FIGS. 3 and 4.

EXAMPLE 5

Release of Dexamethasone from Coated Blue Line Tracheal Tubing

Procedure:

The release of Dexamethasone(LOT #726DK) from polyurethane (Estane BF Goodrich) and EVA (Aldrich) coated tubing was studied. A solution of 5% (w/v) Estane in THF along with a 5% solution of EVA in methylene chloride were first prepared. Dexamethasone was then incorporated into the solution, at ratios of 5 and 10% (w/w) Dexamethasone to Estane and 5, 10 and 20% (w/w) Dexamethasone to EVA. The solutions were then vortexed for 5 minutes. The amount of polymer coating and dexamethasone in the device is summarized in Table 2.

Figure 5:
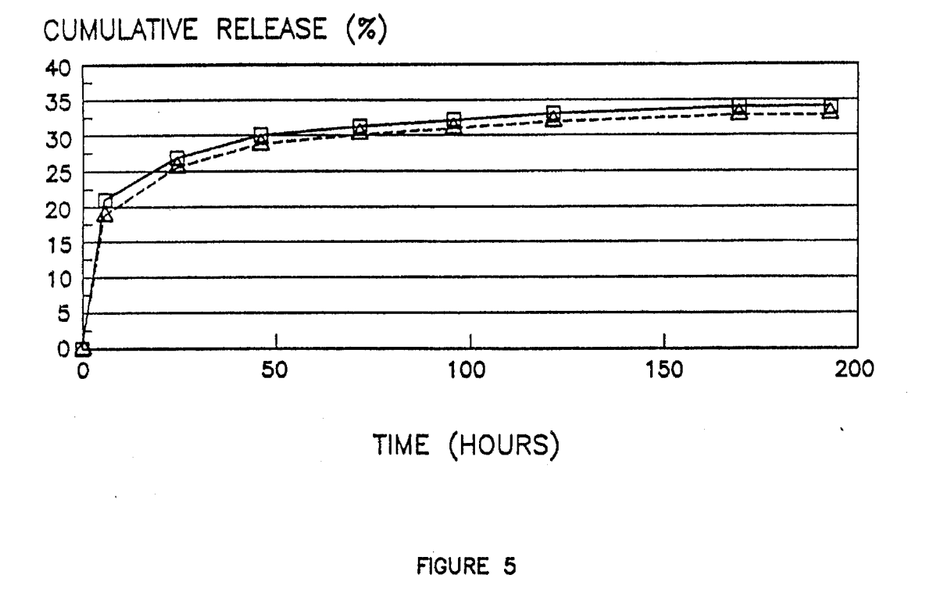
FIG. 5 is a graph of the cumulative percent release of dexamethasone from polyurethane coated tracheal tube over time (hours) for 5% dexamethasone (squares) and 10% dexamethasone (triangle).
Figure 6:
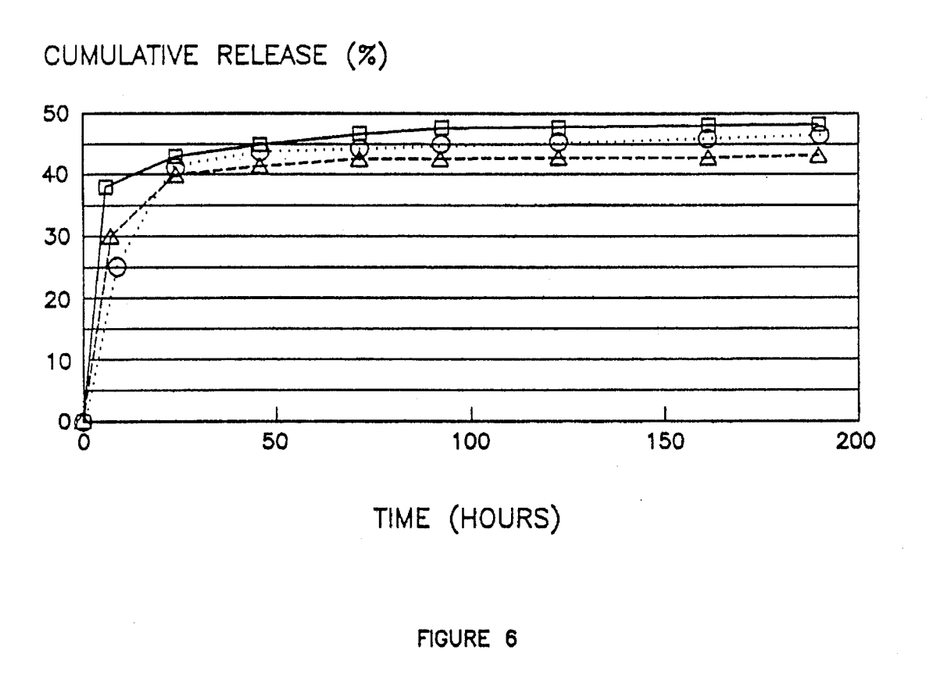
FIG. 6 is a graph of the cumulative percent release of dexamethasone from EVA coated tracheal tube over time (hours) for 5% dexamethasone (squares); 10% dexamethasone (triangle); and 20% dexamethasone (circles).

The tubing (4.115 cm$^2$) was dipped one time into the one of the solutions. Release from ten samples for 190 hours was measured. The release of drug from the coatings is described in FIGS. 5 and 6. The release from both coatings is characterized by an initial release followed by a continuous release of small amounts of drug.

TABLE 2

Relative amounts of Dexamethasone in Estane and EVA coatings.

| Coating | Coating + Dexamethasone mg | Dexamethasone mg |
| --- | --- | --- |
| 5% DEXAMETHASONE IN EVA | 5.8 | .29 |
| 10% DEXAMETHASONE IN EVA | 5.1 | .51 |
| 20% DEXAMETHASONE IN EVA | 4.0 | .80 |
| 5% DEXAMETHASONE IN ESTANE | 9.6 | .48 |
| 10% DEXAMETHASONE IN ESTANE | 10.7 | 1.07 |

EXAMPLE 6

Release of Triamcinolone from Estane Coated Blue Line Tracheal Tubing

Procedure:

A 5% (w/v) solution of Estane in THF was prepared and allowed to stand for 4 hours. Triamcinolone (lot #493rx) was then added to the solution at ratios of 4, 10 and 20% (w/w) Triamcinolone to Estane. The amount of polymer coating and triamcinolone in the device is summarized in Table 3. These solutions were then vortexed for 5 minutes. The tubing (4.115 cm$^2$) was then dipped into the solution one time, and left to cure for 24 hours. Duplicates of the samples were prepared for a total of six samples.

Figure 7:
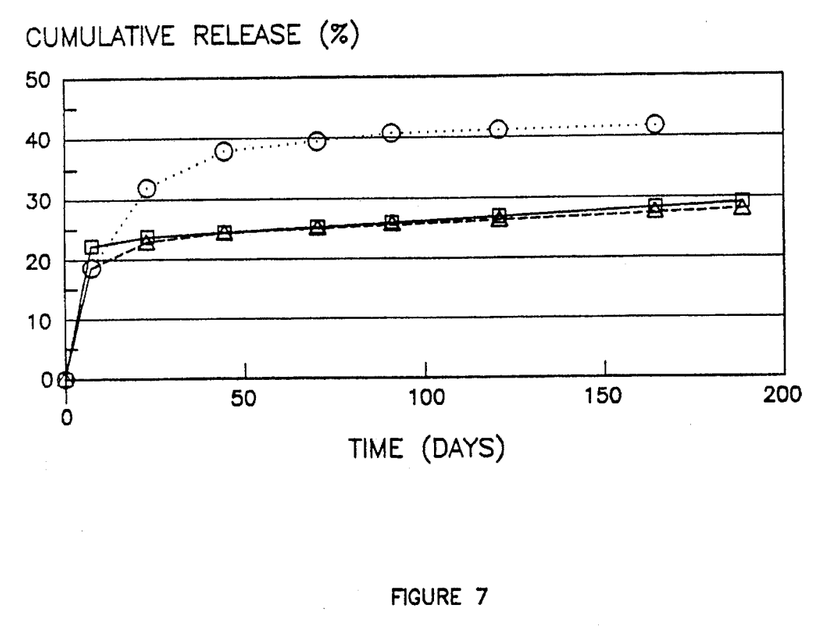
FIG. 7 is a graph of the cumulative percent release of triamcinolone from polyurethane coated tracheal tube over time (days) for 5% triamcinolone (squares); 10% triamcinolone (triangles); and 20% triamcinolone (circles).

The release was followed for several weeks. The data in FIG. 7 shows the release up to 190 hours. As is evident, the release from both coatings is characterized by an initial burst of release followed by a continuous release of small amounts of drug.

TABLE 3

Relative Amounts of Triamcinolone in Estane™ Coatings

| Coating | Coating + Triamcinolone mg | Triamcinolone mg |
| --- | --- | --- |
| 5% TRIAMCINOLONE | 9.1 | .46 |
| 10% TRIAMCINOLONE | 11.8 | 1.18 |
| 20% TRIAMCINOLONE | 6.8 | 1.36 |

EXAMPLE 7

Release of Dexamethasone from Silastic Coated Silicone

Procedure:

Implant Grade Dispersion Silastic (lot #hh090910), 13% Silastic in methyl chloroform, was diluted to 5% using methylene chloride. The solution was left to stand for 4 hours until the solution was homogeneous. To 20 ml of the solution, 5, 10 and 20% (w/w) Dexamethasone (lot #726dk) to Silastic was added. The solution was then vortexed for 5 minutes to ensure a good mixture. The amount of polymer coating and triamcinolone in the device is summarized in Table 4.

TABLE 4

Relative amounts of Dexamethasone in Silastic coated Silicon Tubing

| Coating | Coating + Dexamethasone mg | Dexamethasone mg |
| --- | --- | --- |
| 5% DEXAMETHASONE | 4.4 | .22 |
| 10% DEXAMETHASONE | 3.5 | .35 |
| 20% DEXAMETHASONE | 2.6 | .52 |
| 20% DEXAMETHASONE (3 DIPPINGS) | 8.9 | 1.78 |
| 20% DEXAMETHASONE (ear ventilation tube) | 1.0 | .20 |

Figure 8:
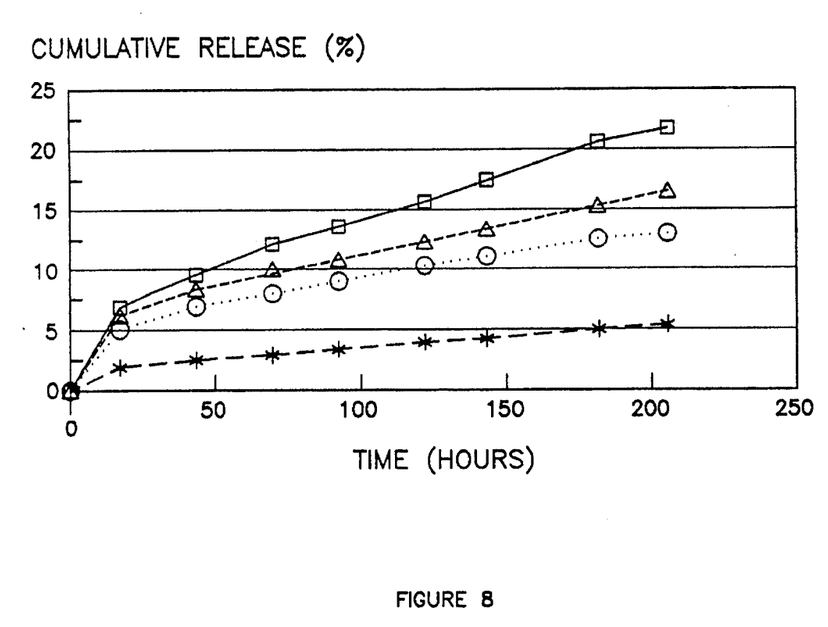
FIG. 8 is a graph of the cumulative percent release of dexamethasone from silastic coated silicone, part of a tracheal device, over time (hours) for 5% dexamethasone (squares); 10% dexamethasone (triangles); 20% dexamethasone (circles); and 20% dexamethasone, three dippings (–*–).
Figure 9:
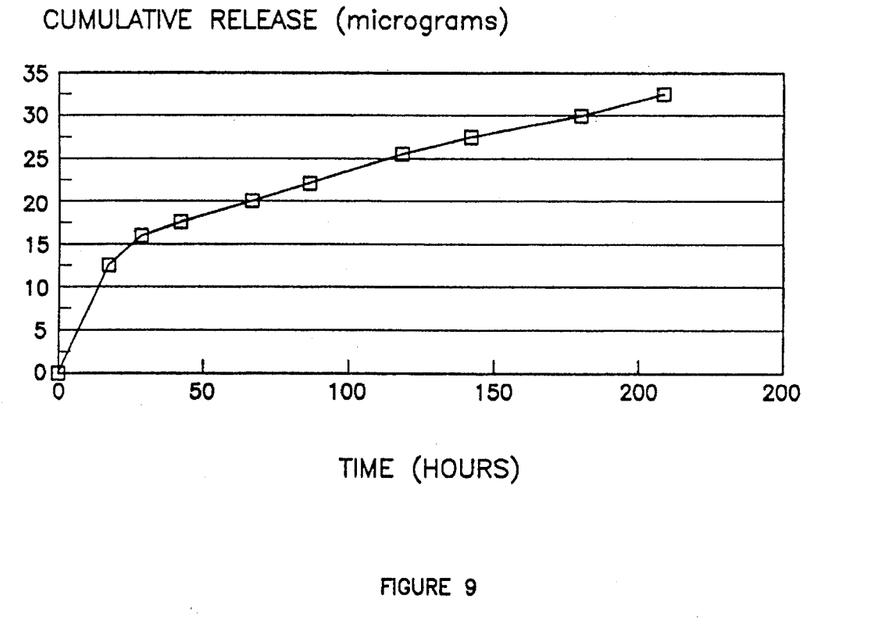
FIG. 9 is a graph of the cumulative percent release of dexamethasone from silastic coated ear ventilation tube (200 μg drug) over time (hours) for 20% dexamethasone (squares).

Two samples of silicone tubing were dipped one time in each of the three solutions. A silicone tube was also dipped three times in the 20% solution, as well as a Xomed Products-ear ventilation device. The release data over 206.5 hours is shown in FIGS. 8 and 9. As is apparent, the release from both coatings is characterized by an initial burst of release followed by a steady release of the drug for a long period of time.

EXAMPLE 8

Release of Triamcinolone from Estane™ Coated Teflon™ Tubing

Procedure:

A solution of 5% (w/v) Estane in THF was prepared by dissolving 1 g of Estane in 20 ml of THF. This solution was allowed to stand for four hours, or until homogeneous. 10 and 20% (w/w) Triamcinolone to Estane was added and the solution was vortexed until uniform. Teflon™ tubing of approximately 2.54 cm in length and 6 mm in diameter was coated by dipping once in the estane™ solution and leaving to dry in the room air. A thin coating of about 0.2 mm which adheres very well to the tubing was produced. One sample of each coating was used in the study, each drying evenly on the surface of the Teflon™. The coating remained intact during the in vitro studies.

Figure 10:
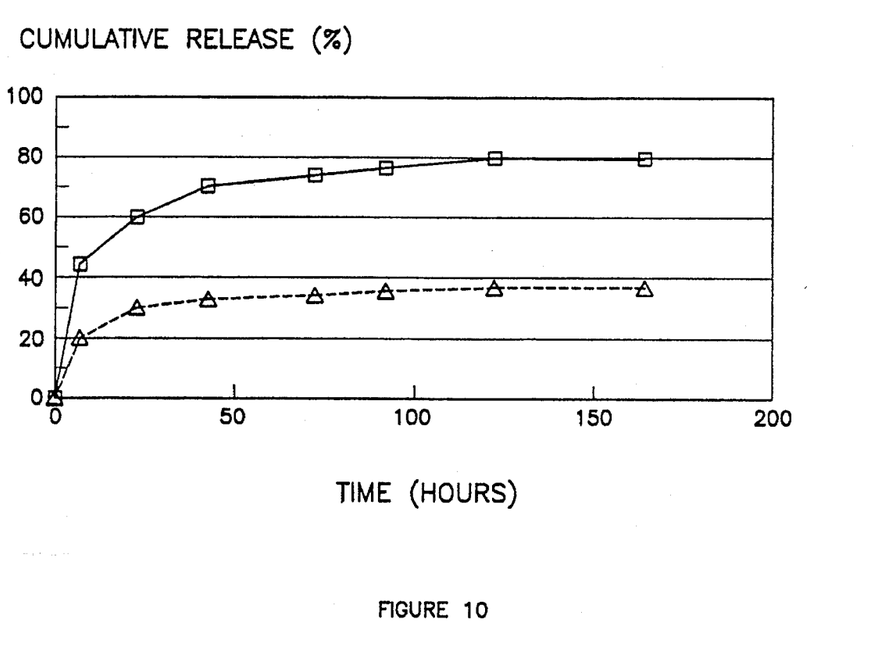
FIG. 10 is a graph of the cumulative release of triamcinolone from polyurethane coated Teflon™ tubing over time (hours) for 10% triamcinolone (squares) and 20% triamcinolone (triangles).

The data showing release through 165 hours is represented in FIG. 10. The amount of polymer coating and triamcinolone in the device is summarized in Table 5. The release of drug from the coatings is described in FIG. 10. As seen, the release from both coatings is characterized by an initial release followed by a steady release of the drug for a long period of time.

TABLE 5

Relative amounts of triamcinolone in Estane™.

| Coating | Coating + Triamcinolone mg | Triamincinolone mg |
|---|---|---|
| 10% TRIAMCINOLONE | 3.8 | .38 |
| 20% TRIAMCINOLONE | 3.2 | .64 |

Modifications and variations of the compositions, and methods for making and using thereof, of the present invention will be obvious to those skilled in the art and are intended to come within the scope of the appended claims.

We claim:

1. A medical device for implantation into tissue comprising, in combination, the device having exterior surfaces, a biocompatible, nonbioerodible polymer dissolved in a solvent to form a solution, the solution being disposed on the exterior surface of the device and the solvent removed to form a uniform coating on the medical device, the polymer coating having a biologically active agent sorbed therein to be released over a period of at least twenty-four hours by diffusion when implanted in the tissue, wherein said biologically active agent is iodine.

2. The medical device of claim 1, wherein the polymer is selected from the group consisting of polyurethane, ethylene vinyl acetate, silicones, hydrogels, and polyvinyl chloride.

3. The medical device of claim 1, further comprising a second polymer coating disposed on the polymer coating having the biologically-active agent sorbed therein, the biologically active agent being absent in the second polymer coating, whereby release of the biologically-active agent by diffusion is further controlled.

4. The medical device of claim 1, wherein the biologically active agent is dissolved in a second solvent to form a second solution, and the polymer coated medical device being immersed in the second solution permitting the biologically active agent to be sorbed in the coating, thereby providing a controlled rapid release of the biologically active agent over a period of at least twenty-four hours.

5. The medical device of claim 1, wherein the solvent is selected from the group consisting of dichloromethane, tetrahydrofuran, methylene chloride and methyl chloroform.

6. A medical device for implantation into tissue comprising, in combination, the device having exterior surfaces, a biocompatible, nonbioerodible polymer dissolved in a solvent to form a solution, a biologically active agent dissolved in said solution, the solution being disposed on the exterior surface of the device, and the solvent removed to form a uniform coating on the medical device such that polymer coating having the biologically active agent solvent casted therein is released by diffusion over a period of at least two days when implanted in the tissue, wherein said biologically active agent is iodine.

7. The medical device of claim 6, wherein the polymer is selected from the group consisting of polyurethane, ethylene vinyl acetate, silicones, hydrogels, and polyvinyl chloride.

8. The medical device of claim 6, further comprising a second polymer coating disposed on the polymer coating having the biologically-active agent solvent casted therein the biologically active agent being absent in the second polymer coating, whereby release of the biologically-active agent by diffusion is further controlled.

9. A medical device for implantation into tissue comprising, in combination, the device having exterior surfaces, a biocompatible, nonbioerodible polymer, being dissolved in a solvent to form a solution, the solution further having a biologically active agent dissolved therein, the solution being disposed on the device, the solvent being removed and forming a single uniform coating on the device wherein the biologically active agent is released by diffusion when the coated device is in contact with the tissue, said release being controlled over a period of at least twenty-four hours and wherein said biologically active agent is iodine.

* * * * *

UNITED STATES PATENT AND TRADEMARK OFFICE
CERTIFICATE OF CORRECTION

PATENT NO. : 5,512,055
DATED : April 30, 1996
INVENTOR(S) : Shikani et al

It is certified that error appears in the above-indentified patent and that said Letters Patent is hereby corrected as shown below:

On title page, change the inventors section as follows:

"[75] Inventors: Abraham J. Domb; Alain Shikani; Andrew S. T. Haffer; Manoj Maniar, all of Baltimore, Md."

should read

--[75] Alain H. Shikani, Ruxton, MD; Abraham J. Domb, Efrat, ISRAEL; Andrew S. T. Haffer, Baltimore, MD; Manoj Maniar, Baltimore, MD--

Signed and Sealed this

Seventeenth Day of September, 1996

Attest:

BRUCE LEHMAN

*Attesting Officer*  *Commissioner of Patents and Trademarks*